United States Patent

Blaustein et al.

[11] Patent Number: 6,000,083
[45] Date of Patent: Dec. 14, 1999

[54] ELECTRIC TOOTHBRUSH

[75] Inventors: Lawrence A. Blaustein, Moreland Hills; John R. Nottingham, Hunting Valley; John Osher, Moreland Hills; John W. Spirk, Gates Mills, all of Ohio

[73] Assignee: Dr. Johns Products, Ltd., Bedford Heights, Ohio

[21] Appl. No.: 09/163,621

[22] Filed: Sep. 30, 1998

[51] Int. Cl.⁶ .................................................. A46B 13/02
[52] U.S. Cl. .............................................. 15/28; 15/22.1
[58] Field of Search .......................... 15/22.1, 22.2, 15/28, 22.4, 23, 24, 29

[56] References Cited

U.S. PATENT DOCUMENTS

| | | | |
|---|---|---|---|
| 3,775,800 | 12/1973 | Veneziani ..................................... | 15/28 |
| 4,203,431 | 5/1980 | Abura et al. ................................. | 15/28 |
| 5,070,567 | 12/1991 | Holland . | |
| 5,120,225 | 6/1992 | Amit ......................................... | 15/22.1 |
| 5,170,525 | 12/1992 | Cafaro ........................................ | 15/28 |
| 5,186,627 | 2/1993 | Amit et al. . | |
| 5,274,870 | 1/1994 | Stollman . | |
| 5,341,534 | 8/1994 | Serbinski et al. . | |
| 5,378,153 | 1/1995 | Giuliani et al. . | |
| 5,590,434 | 1/1997 | Imai . | |
| 5,732,433 | 3/1998 | Göcking et al. . | |

*Primary Examiner*—Randall E. Chin
*Attorney, Agent, or Firm*—Fay, Sharpe, Fagan, Minnich & McKee

[57] ABSTRACT

An electric toothbrush comprising an elongated body portion and a head including a static portion and a circular portion, a handle, and an angled shaft between the head and the handle. The circular portion rotates or oscillates about an axis normal to a longitudinal axis of the head. The circular portion includes stiff bristles and the static portion includes soft bristles. The stiff bristles are recessed with respect to the soft bristles. The elongated body portion is hollow and further includes a motor in the hollow portion, which is operatively connected to the circular portion for rotating or oscillating the circular portion. A switch is operatively connected to the motor to provide momentary and continuous operation of the toothbrush. A worm gear and a pair of step gears are located in the hollow portion. The motor is operatively connected to the worm gear and the step gears are operatively connected to the worm gear and to each other. One of the step gears is offset with respect to a longitudinal axis of the elongated body portion. A shaft which is operatively connected to the offset step gear and to a second end to the circular portion. A battery is located within the hollow section for powering the motor.

10 Claims, 8 Drawing Sheets

ELECTRIC TOOTHBRUSH

BACKGROUND OF THE INVENTION

The present invention relates generally to electric toothbrushes. More particularly, it relates to an improved battery powered toothbrush.

The benefits of brushing one's teeth using motorized toothbrushes are well known, and motorized movement in toothbrushes has been the subject of much recent innovation and design activity. Also, the commercial market has seen the introduction, over the last several years, of many different types of motorized toothbrushes. However, an examination of the available technology shows, a tendency toward increasingly complex, expensive, and non-commercially feasible methods of achieving motorized motions in the bristles and heads of toothbrushes to aid in more effectively cleaning one's teeth.

The commercial marketplace has become divided into two price markets. On the higher priced end are some of these more complex motorized toothbrushes that provide various motions to the bristles and brush head. The lower end of the market has become the province of very simple motorized toothbrushes that only vibrate through the use of an offset weight attached to the motor shaft, and which provide very little true additional cleaning benefit with their use, since no vigorous motion is transmitted to the cleaning surface of the brush. The vibrations are also very uncomfortable to the hand and act as a disincentive to brush one's teeth for an adequate time.

Numerous electric toothbrushes have been developed over the years. Some known devices are shown in U.S. Pat. No. 5,070,567; U.S. Pat. No. 5,186,627; U.S. Pat. No. 5,274,870; U.S. Pat. No. 5,341,534; U.S. Pat. No. 5,378,153; and U.S. Pat. No. 5,732,433.

The intention of the present invention is to provide a low cost, effective, ergonomically correct, motorized toothbrush wherein the brush includes both a moving circular brush portion and a fixed brush portion.

Accordingly it has been considered desirable to develop a new and improved electric toothbrush which would overcome the foregoing difficulties and others while providing better and more advantageous overall results.

SUMMARY OF THE INVENTION

The present invention relates to an electric toothbrush.

More specifically, the electric toothbrush is used in personal hygiene to clean one's teeth and gums using a motorized movement.

The electric toothbrush includes an elongated body portion, a brush head attached to a first end of the elongated body portion, a handle attached to a second end of the elongated body portion, and an angled shaft between the brush head and the handle.

The brush head includes a longitudinal axis, a circular portion and a static portion. The circular portion rotates or oscillates about an axis normal to the longitudinal axis of the brush head and is incorporated into the larger brush head. The brush head also includes static bristles located about the circular portion. The stiff bristles of the circular portion are slightly recessed in height from the static bristles. This particular arrangement allows for the circular portion to include stiff bristles which will aid in the deep cleaning and plaque removal process, while the stationary bristles would typically consist of a softer bristle, so as riot to damage the gums.

The brush head has a more traditional larger brush head shape which permits the user to brush his teeth in the typical manner of an up and down fashion, while a motorized circular portion of the brush head cleans more effectively. The design of the brush head allows for inexpensive manufacture and brings effective motorized rotational toothbrushes within the financial reach of a larger portion of the population.

The angled shaft provides an ergonomic benefit that has not been utilized on a motorized toothbrush. The angle is well known for its ergonomic benefit in permitting easier access into the back recesses of the mouth while still contacting the tooth surface.

The elongated body portion includes a hollow portion. The toothbrush is further comprised of a motor within the hollow portion of the elongated body portion. The motor is operably connected to the circular portion of the brush head for rotating or oscillating the stiff bristles on the head. The motor has a longitudinal axis which is coaxial with a longitudinal axis of the elongated body portion.

The hollow portion further includes a simplified gear assembly. The gear assembly includes a worm gear, two step gears and a shaft. The motor is operatively connected to the worm gear. The step gears are operatively connected to the worm gear and to each other. The gear assembly delivers sufficient torque, speed, and battery longevity. The first step gear permits a second matching step gear to be offset with respect to a longitudinal axis of the elongated body portion and placed at the desired angle so that the shaft itself can still be straight, thus losing no power or torque through the added friction of a flexible shaft. The shaft is operatively connected at a first end to the offset step gear and at a second end to the circular portion of the brush head.

The body further includes a switch to allow operation of the unit. The switch includes an actuator button and a metal contact. The switch is manually depressed by pressing a molded actuator button down, which presses against a metal contact, completing the circuit, as in a conventional momentary switch. The switch allows continuous operation, through a ramp design, by depressing and sliding the actuator button forward as in a conventional continuous switch. The forward motion, combined with the molded in ramp, causes the actuator button to move downward, pressing against the metal contact, and completing the circuit. By combining these two functions in one switch, the consumer can try the unit and see its operation prior to purchase, and still operate it continuously once out of the package.

The electric toothbrush can further include a battery located within the hollow portion of the elongated body portion. A slidable, snap-on cover is depressed then released from the end of the handle and opens to expose the hollow portion. The battery is then inserted and then the cover is slid into position and snapped into place.

One advantage of the present invention is the provision of an electric toothbrush with a brush head with a traditional larger brush head shape to permit the user to brush teeth in an up and down fashion.

Another advantage of the present invention is the provision of an electric toothbrush which is easy and inexpensive to manufacture.

Another advantage of the present invention is the provision of an electric toothbrush with an angled shaft to permit easier access to the back of the user's mouth.

Still another advantage of the present invention is the provision of an electric toothbrush with a static portion and a circular portion that rotates or oscillates.

Yet another advantage of the present invention is the provision of an electric toothbrush with a switch which allows momentary operation or continuous operation of the toothbrush.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, preferred embodiments of which will be described in detail in this specification and illustrated in the accompanying drawings which form a part hereof, and wherein.

DETAILED DESCRIPTION OF THE PREFERRED EMBODIMENT

Figure 1:
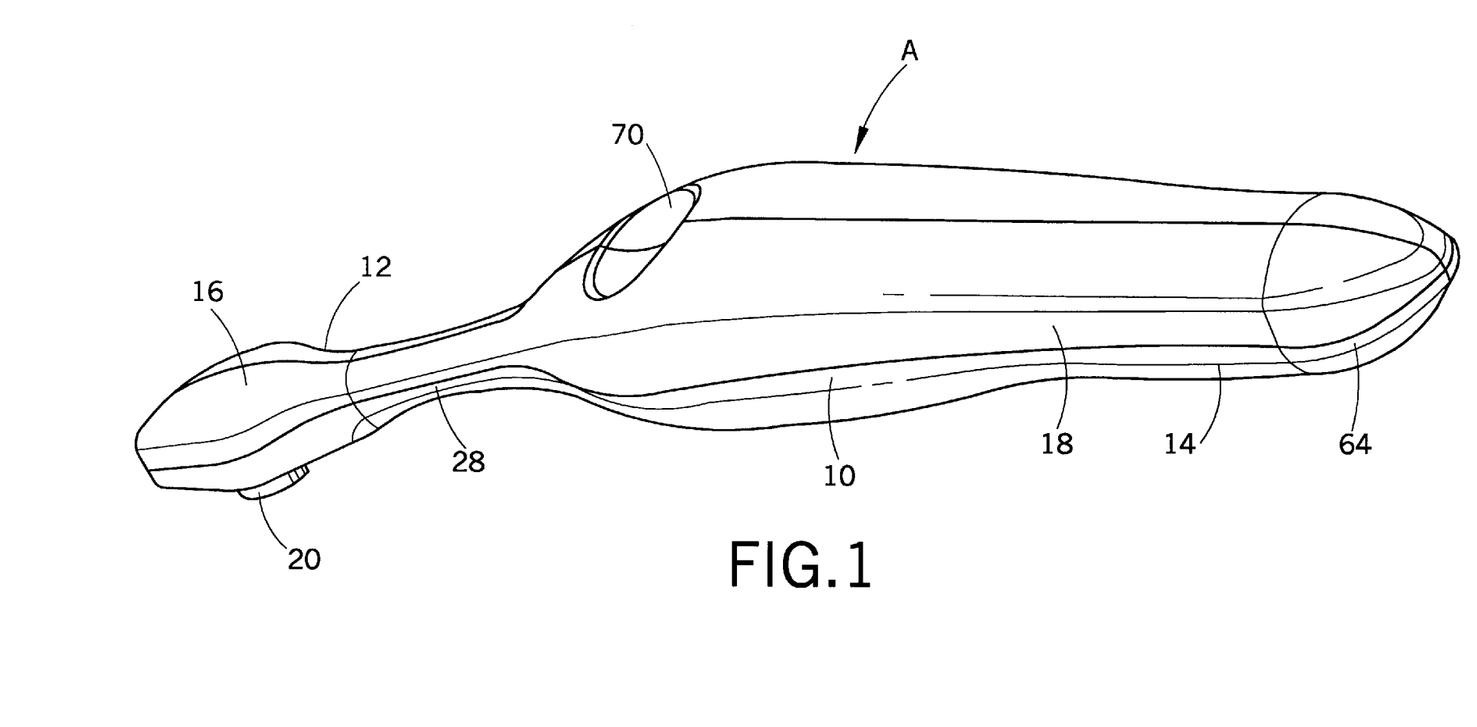
FIG. 1 is a perspective view of the electric toothbrush in accordance with a preferred embodiment of the present invention.

Referring now to the drawings wherein the showings are for the purposes of illustrating the preferred embodiment of the invention only and not for purposes of limiting same, FIG. 1 shows an electric toothbrush A according to the present invention. The electric toothbrush can be used for personal hygiene such as brushing one's teeth and gums.

As shown in FIG. 1, the electric toothbrush includes an elongated body portion 10, which has a first end 12 and a second end 14. A head 16 is attached to the first end 12 and a handle 18 is attached to the second end 14.

Figure 2:
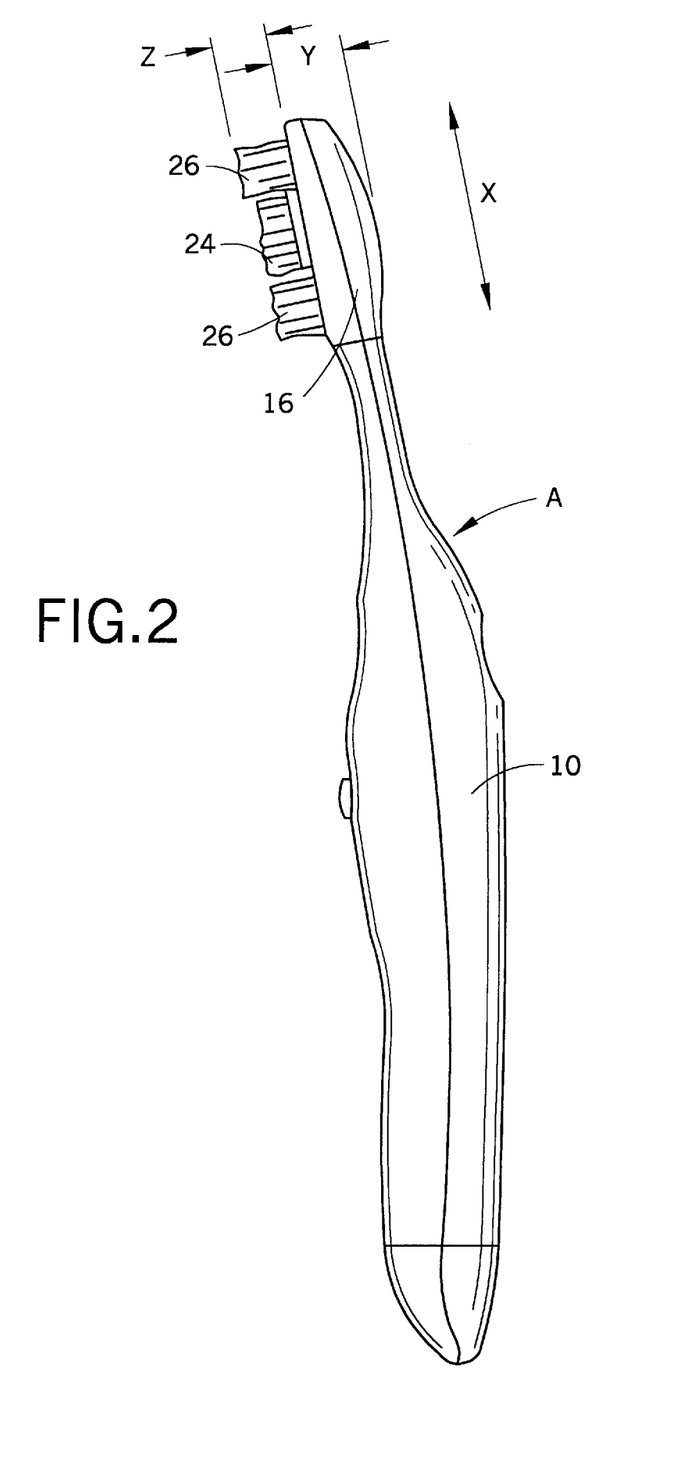
FIG. 2 is a side elevational view of the electric toothbrush of FIG. 1.

The head 16 has a more traditional larger brush head shape which permits the user to brush his teeth in the typical manner of an up and down fashion. As shown on FIG. 2, the length of the head 16, dimension "X", can range from about 0.75 inches to about 1.75 inches. The thickness of the brush head, dimension "Y", can range from about 0.25 inches to about 0.50 inches. The design of the head 16 allows for inexpensive manufacture and assists in bringing effective motorized rotational toothbrushes within the financial reach of a large portion of the population.

Figure 3:
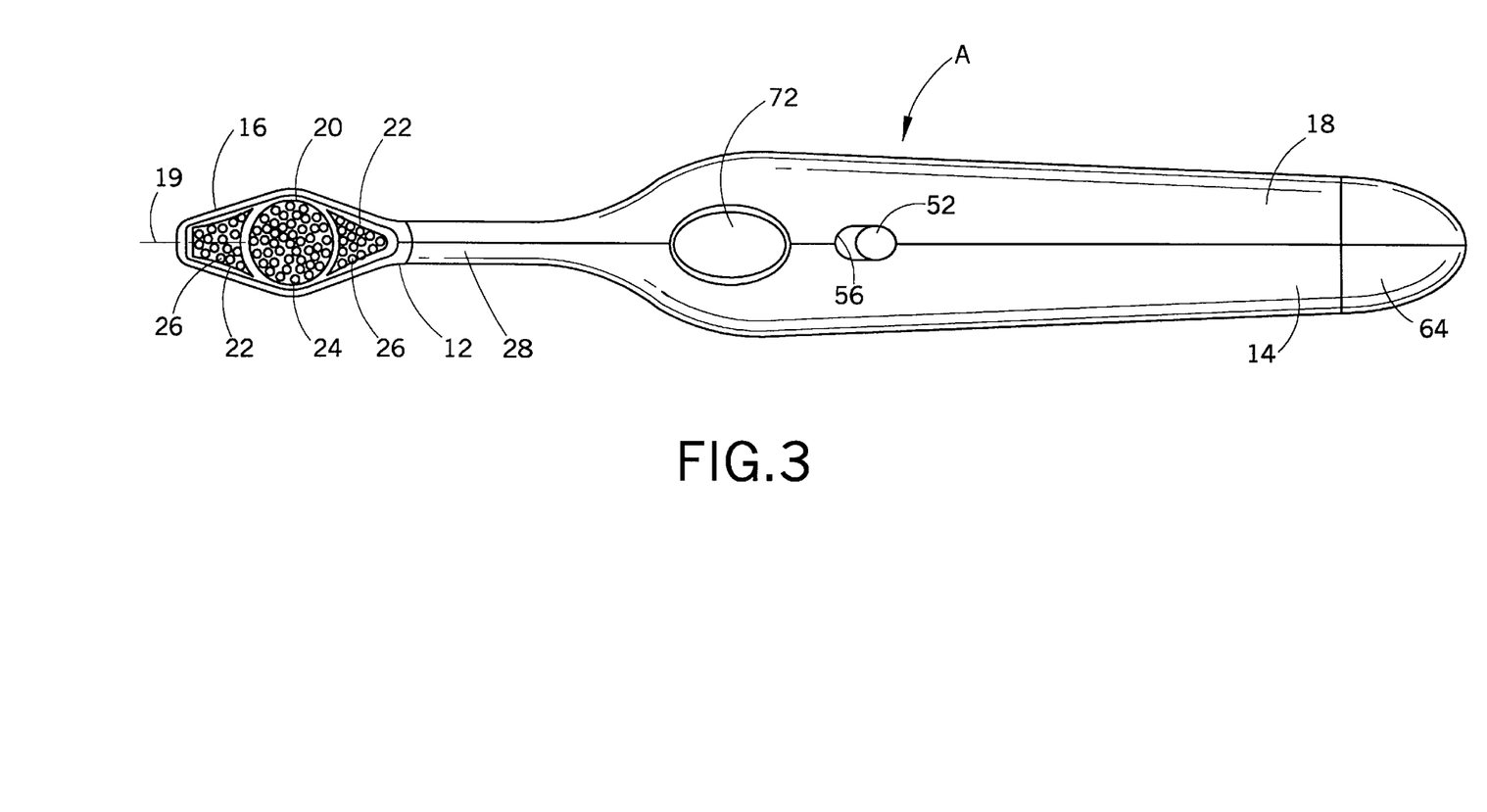
FIG. 3 is a bottom elevational view of the electric toothbrush.

Referring now to FIG. 3, the head 16 further includes a longitudinal axis 19, a circular or moving portion or brush head 20 and a static portion or brush head 22. The static portion 22 is located on opposite sides of the circular portion 20. The circular portion 20 is located at the center of the head 16. The circular portion 20 rotates or oscillates about an axis approximately normal to the longitudinal axis 19 of the brush head 16. The circular portion 20 includes stiff bristles 24. The static portion 22 includes soft bristles 26.

The stiff bristles 24 are slightly recessed with respect to the soft bristles 26. The stiff bristles 24 aid in the deep cleaning and plaque removal process, while the stationary soft bristles 26 are softer so as to not damage the gums. The thickness of the bristles, dimension "Z", shown in FIG. 2, can range from about 0.25 inches to about 0.75 inches.

Referring again to FIG. 3, the elongated body portion 10 further includes an angled shaft 28, located between the head 16 and the handle 18. The angled shaft 28 provides an ergonomic benefit that has not been utilized on a motorized toothbrush. The angle is well known for its ergonomic benefit in permitting easier access into the back recesses of the mouth while still contacting the tooth surface.

Figure 4:
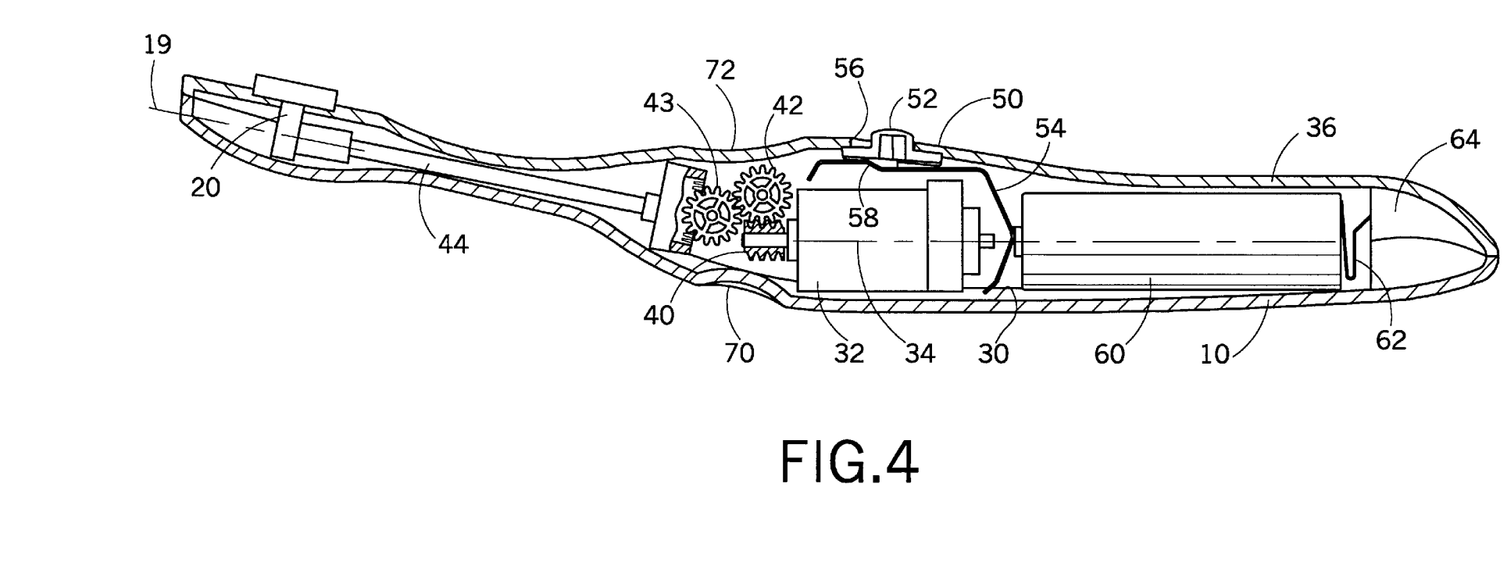
FIG. 4 is a side elevational view in cross section of the electric toothbrush of FIG. 1.
Figure 5:
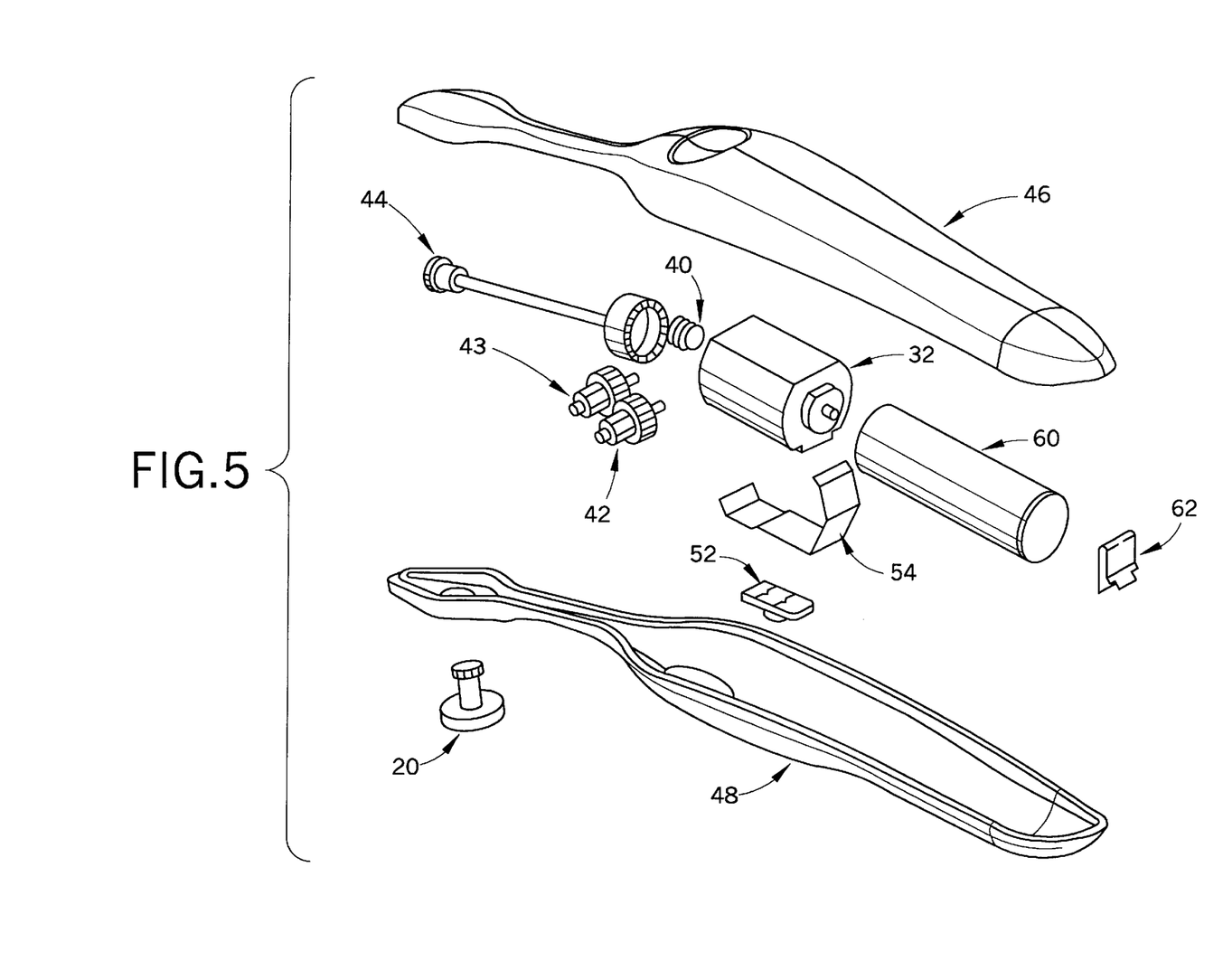
FIG. 5 is an exploded perspective view of the electric toothbrush of FIG. 1.

As shown in FIG. 4 and FIG. 5, the elongated body portion 10 further includes a hollow portion 30 which houses a motor 32. The motor 32 has a longitudinal axis 34 in line with a longitudinal axis 36 of the elongated body portion 10.

To provide power to the circular portion 20 to rotate or oscillate, the motor 32 powers a worm gear 40 and a pair of step gears 42, 43. The motor 32 is operatively connected to the worm gear 40. Step gear 42 is operatively connected to step gear 43 and the worm gear 40.

Figure 6:
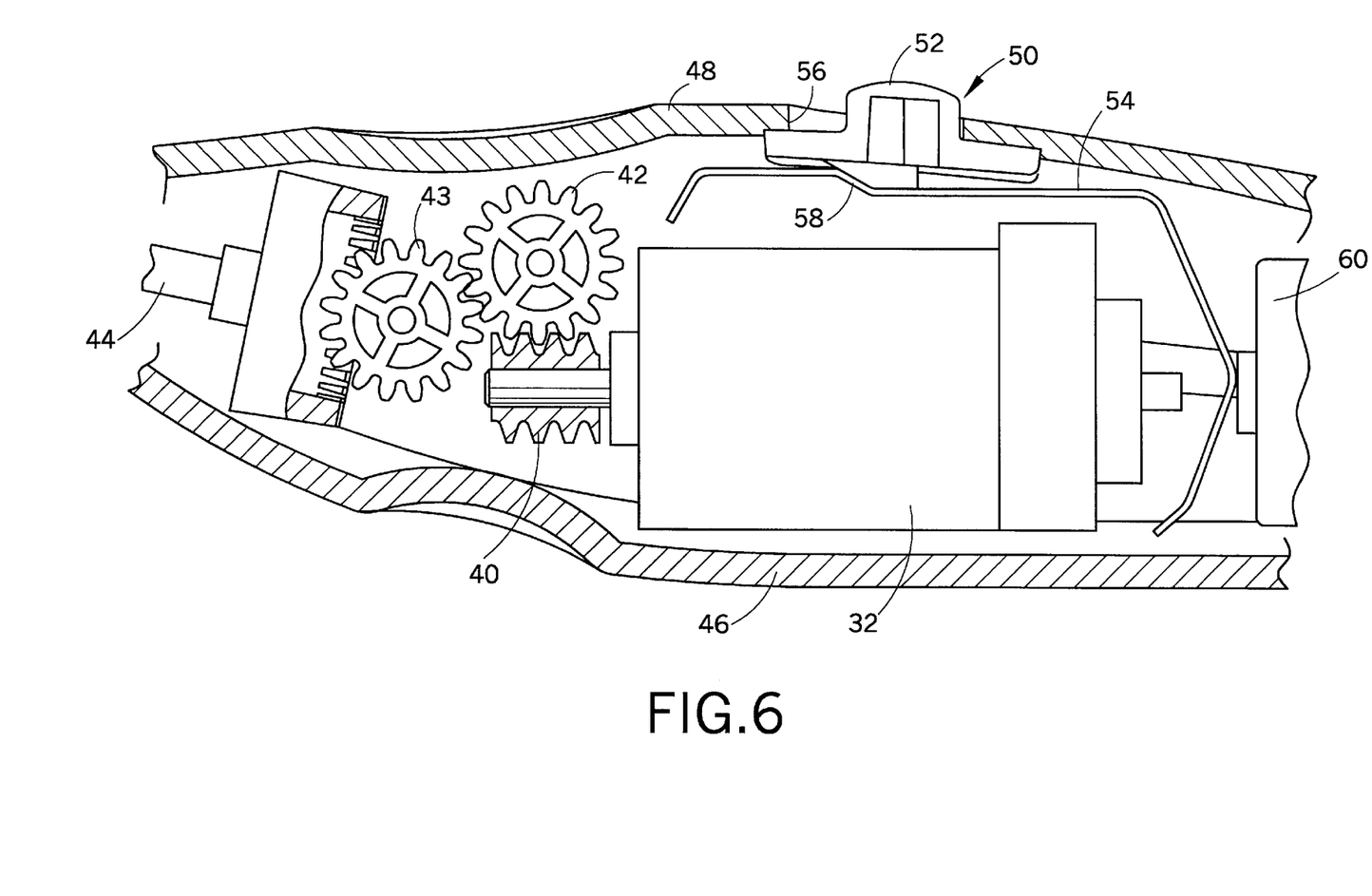
FIG. 6 is an enlarged side elevational view in cross section of the motor and gear assembly of the electric toothbrush of FIG. 1.

As shown in FIG. 4 and FIG. 6, the first step gear 42 permits the matching second step gear 43 to be offset with respect to the longitudinal axis 36 of the elongated body portion 10.

Figure 7:
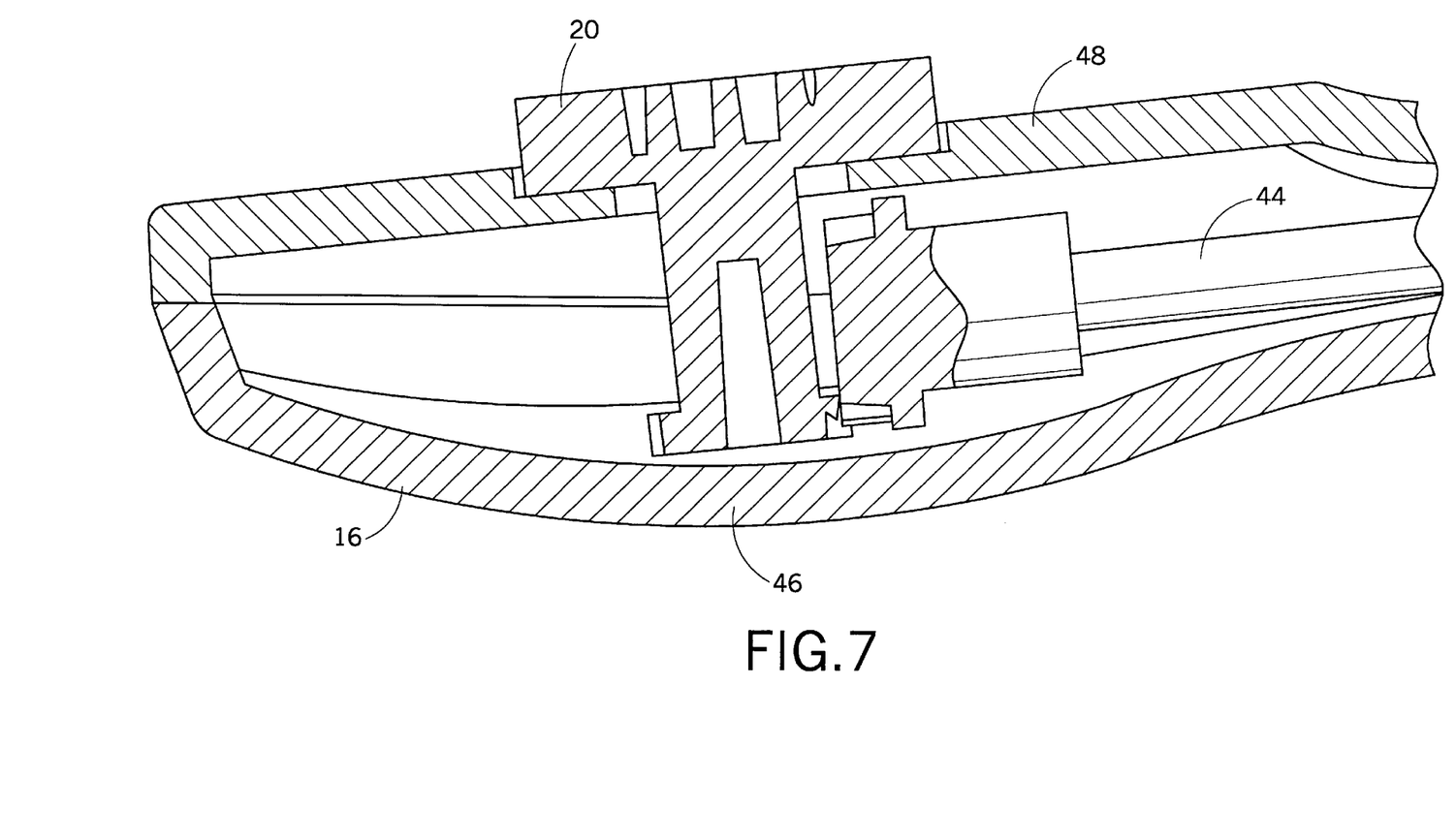
FIG. 7 is an enlarged side elevational view in cross section of the head of the electric toothbrush of FIG. 1; and, FIG. 8 is a front and side elevational view of the electric toothbrush in packaging.

As shown in FIGS. 4, 6 and 7, an elongated shaft 44 is connected at a first end to the offset step gear 43 and at a second end to the circular portion 20. The second step gear 43 is placed at a desired angle so that the shaft 44 itself can still be straight, thus losing no power or torque through the added function of a flexible shaft.

Referring again to FIG. 5, the motor 32 and gears 40, 42, 43 are housed with an upper housing 46 and a lower housing 48.

Referring again to FIG. 4, a switch 50 is provided to control operation of the electric toothbrush and is operatively connected to the motor 32. The switch 50 includes a molded actuator button 52 and a metal contact 54. The switch 50 is manually depressed by pressing a molded actuator button 52 down, which then presses against a metal contact 54, which completes the circuit and provides momentary operation of the toothbrush. The switch 50 also allows continuous operation through a ramp design, sliding the button 52 forward toward the head 16 to provide for continuous operation. Moving the button 52 forward, combined with a molded in ramp 58 in the metal contact 54, causes the button 52 to move downward, pressing against the metal contact 54 and completing the circuit. The toothbrush then continuously operates until the button 52 is slid back into an off position toward the handle 18 and the button 52 disengages the metal contact 54.

Figure 8:
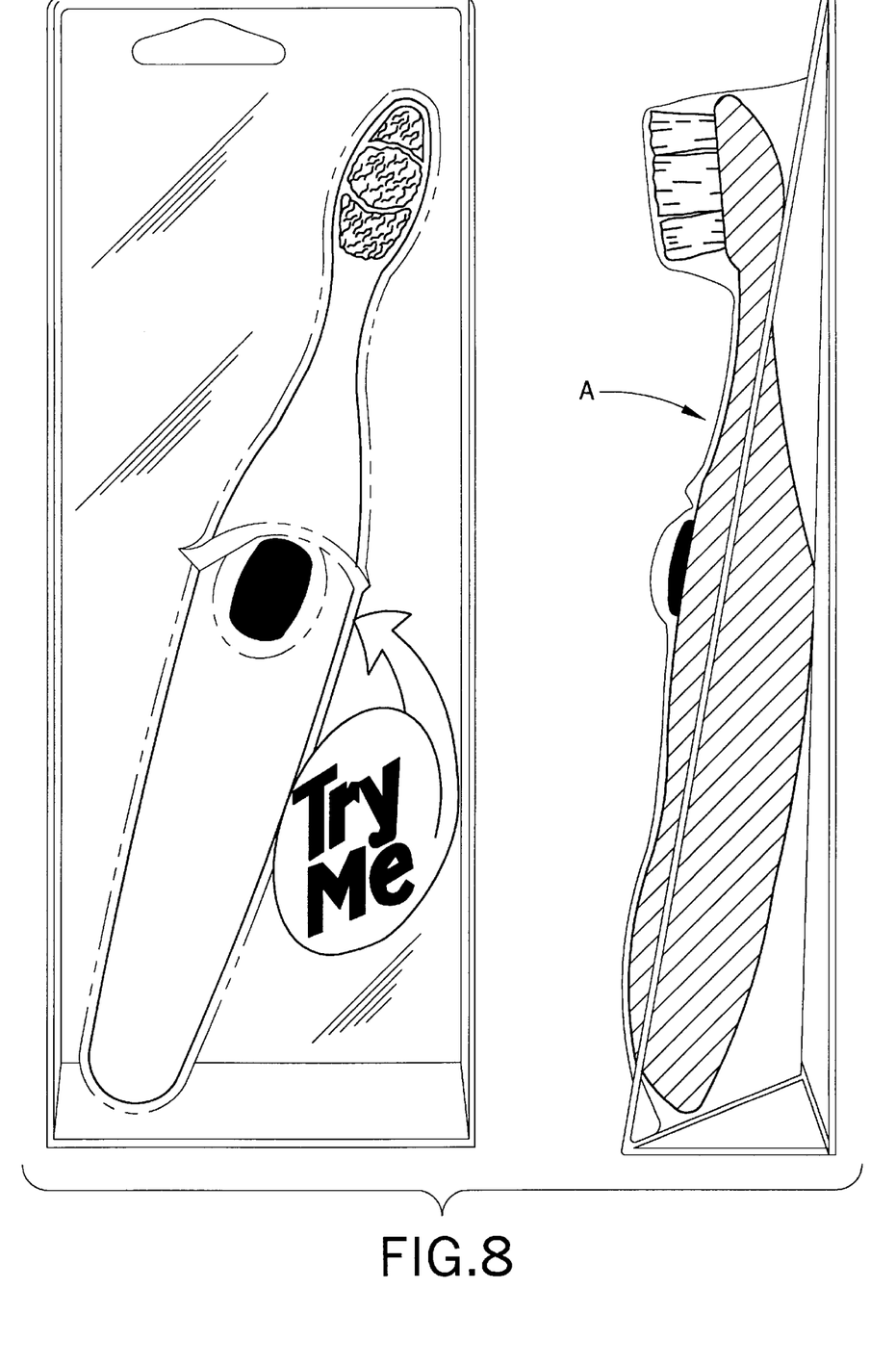

By combining these two functions in one switch 50, the toothbrush can be packaged in packaging as shown in FIG. 8 where the consumer can depress the button 52 through the packaging and see its operation while still inside the packaging, and then be able to operate it continuously once out of the package. FIG. 8 illustrates one version of the button 52. It should be noted that other sizes and shapes of buttons may be used.

Referring now to FIGS. 4 and 5, a battery 60 is provided within the hollow portion 30 of the elongated body portion 10. A battery terminal or contact 62 is provided for the battery 60. An AA battery can be used as is illustrated in FIG. 4. To install the battery 60 into the hollow portion 30, a slidable snap-on cover 64 is depressed and slid off the end of the handle 18 to expose the hollow portion 30. The battery 60 is inserted, then the cover 64 is slid back on to the housing and snapped into place. The terminal end of the battery 60 is then in contact with the metal contact 54.

If desired, depressions or grip areas 70 and 72 can be molded into the upper and lower housings 46, 48 as shown in FIG. 4. The depressions 70, 72 are used to support a user's thumb and forefinger or other fingers to make using the electric toothbrush easier and more comfortable.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. An electric toothbrush comprising:

an elongated body having a handle portion, a head portion, and an elongated body shaft portion intermediate the handle portion and the head portion and wherein the elongated body shaft portion has a smaller cross-sectional dimension than the handle portion, the head portion including static and moving bristles, the head portion and body shaft portions being dimensioned for disposition in a human user's mouth for brushing of teeth; and a motor disposed in the handle portion and operatively connected to the moving bristles with a gearing and shaft assembly including an elongated shaft closely received in and extending along at least a portion of the length of the body shaft portion for driving the moving bristles.

2. The electric toothbrush of claim 1 wherein the moving bristles include stiff bristles and the static bristles include soft bristles.

3. The electric toothbrush of claim 2 wherein the stiff bristles are recessed with respect to the soft bristles.

4. The electric toothbrush of claim 1 further including a switch operatively connected to said motor which provides momentary and continuous operation of the toothbrush.

5. The electric toothbrush of claim 4 further comprising a worm gear and a pair of step gears located in said hollow portion, wherein said motor is operatively connected to said worm gear and said step gears are operatively connected to said worm gear and to each other.

6. The electric toothbrush of claim 5 wherein said elongated body includes longitudinal axis and one of said step gears is offset with respect to said longitudinal axis.

7. The electric toothbrush of claim 6 further comprising a shaft located within said angled shaft and which is operatively connected at a first end to said offset step gear and at a second end to said moving bristles.

8. The electric toothbrush of claim 7 further including a battery located within said handle portion for powering said motor.

9. The electric toothbrush of claim 1 wherein said moving bristles comprise rotating bristles.

10. The electric toothbrush of claim 1 wherein said moving bristles comprise oscillating bristles.

* * * * *